United States Patent
Sunley

(10) Patent No.: US 8,445,741 B2
(45) Date of Patent: May 21, 2013

(54) PROCESS FOR THE PRODUCTION OF HYDROCARBONS

(75) Inventor: John Glenn Sunley, Cottingham (GB)

(73) Assignee: BP Oil International Limited, Middlesex (GB)

( * ) Notice: Subject to any disclaimer, the term of this patent is extended or adjusted under 35 U.S.C. 154(b) by 725 days.

(21) Appl. No.: 12/310,779

(22) PCT Filed: Aug. 29, 2007

(86) PCT No.: PCT/GB2007/003266
§ 371 (c)(1),
(2), (4) Date: Mar. 6, 2009

(87) PCT Pub. No.: WO2008/032015
PCT Pub. Date: Mar. 20, 2008

(65) Prior Publication Data
US 2009/0203949 A1 Aug. 13, 2009

(30) Foreign Application Priority Data
Sep. 12, 2006 (EP) .................................. 06254749

(51) Int. Cl.
*C07C 2/86* (2006.01)
(52) U.S. Cl.
USPC ........... 585/639; 585/638; 585/641; 585/642; 585/733
(58) Field of Classification Search ................. 585/638, 585/639, 640, 641, 642, 500, 733
See application file for complete search history.

(56) References Cited

U.S. PATENT DOCUMENTS

| | | | | |
|---|---|---|---|---|
| 3,697,611 A | * | 10/1972 | Magoon | 585/637 |
| 4,151,214 A | | 4/1979 | Kim et al. | |
| 4,377,503 A | * | 3/1983 | Dessau | 502/77 |
| 4,690,912 A | * | 9/1987 | Paulik et al. | 502/161 |
| 6,066,762 A | * | 5/2000 | Yoneda et al. | 562/519 |

FOREIGN PATENT DOCUMENTS

| WO | WO 02/070440 A1 | * 9/2002 |
|---|---|---|
| WO | WO 2005/023733 | 3/2005 |

OTHER PUBLICATIONS

Fabre, et al., "Generation of Alkyl(dicarbonyl)(chloro)Ruthenium Dimers in the Ruthenium-Catalyzed Addition of Alkyl Formates to Ethylene" in Angew. Chem. Int. Ed. Engl., 1997, 36(10), 1092-1095—month unknown.*
White, et al., "Ruthenium: Organometallic Chemistry" in Encyclopedia of Inorganic Chemistry, John Wiley & Sons, 2006, available on-line Mar. 15, 2006.*
Sakamuri, "Esters, Organic" in Kirk-Othmer Encyclopedia of Chemical Technology, J. Wiley & Sons, available on-line Dec. 19, 2003.*
Griesbaum, et al., "Hydrocarbons" in Ullmann's Encyclopedia of Industrial Chemistry, Wiley-VCH, available on-line Jun. 15, 2000.*
Written Opinion of the International Search Report for PCT/GB2007/003266, mailed Dec. 14, 2007.

* cited by examiner

*Primary Examiner* — In Suk Bullock
*Assistant Examiner* — Bradley Etherton
(74) *Attorney, Agent, or Firm* — Nixon & Vanderhye

(57) ABSTRACT

Process for the production of a hydrocarbon by reacting, in a reactor, a reactant selected from methanol, dimethyl ether, methyl acetate and mixtures thereof, with an olefin. The process is performed in the presence of methyl halide and/or hydrogen halide and at least one compound selected from ruthenium carbonyl halides, osmium carbonyl halides and mixtures thereof.

16 Claims, No Drawings

PROCESS FOR THE PRODUCTION OF HYDROCARBONS

This application is the U.S. national phase of International Application No. PCT/GB2007/003266, filed 29 Aug. 2007, which designated the U.S. and claims priority to Europe Application No. 06254749.2, filed 12 Sep. 2006, the entire contents of each of which are hereby incorporated by reference.

This invention relates to a process for the production of hydrocarbons and in particular to a process for the production of a hydrocarbon by the reaction of a reactant selected from the group consisting of methanol, dimethyl ether, methyl acetate and mixtures thereof with an olefin.

Hydrocarbons may be produced by methylation. Methylation of olefins involves the introduction of a methyl group into an olefin to produce a hydrocarbon with one more carbon atom than the starting olefin. Thus, if the olefin already contains one or more methyl branches, methylation involves introducing one or more additional methyl branches. Methylation may be useful to convert one hydrocarbon into another, more useful hydrocarbon. Methylation may be used to produce hydrocarbons which are beneficial as components in fuels.

Thus, U.S. Pat. No. 4,151,214 relates to the reaction of an olefin with methanol, dimethyl ether or mixtures thereof in the presence of zinc iodide, zinc bromide or mixtures thereof at a temperature of 180 to 450° C. In particular, U.S. Pat. No. 4,151,214 describes the reaction of 2,3-dimethyl-2-butene with methanol in the presence of zinc iodide to produce a reaction product comprising 2,3-dimethyl-1-butene; 2,3-dimethyl-2-butene; 2,3,3-trimethylbut-1-ene (triptene); 2,2,3-trimethylbutane (triptane); $C_{12}H_{24}$ and other branched hydrocarbons. This process is not entirely satisfactory, for example it is not particularly selective.

A branched hydrocarbon such as triptane (2,2,3-trimethylbutane) is useful as a gasoline component and may be produced from methanol and/or dimethyl ether. Thus, international patent publication WO2005/023733 relates to a process for producing branched chain hydrocarbons from methanol and/or dimethyl ether using an indium halide catalyst.

There remains a need for an alternative process for the production of a hydrocarbon by the reaction of methanol and/or dimethyl ether with an olefin.

Thus, according to the present invention there is provided a process for the production of a hydrocarbon which process comprises reacting, in a reactor, a reactant selected from the group consisting of methanol, dimethyl ether, methyl acetate and mixtures thereof, with an olefin in the presence of methyl halide and/or hydrogen halide and at least one compound selected from the group consisting of ruthenium carbonyl halides, osmium carbonyl halides and mixtures thereof.

Each ruthenium carbonyl halide or osmium carbonyl halide may have an empirical formula:

in which:
M is Ru or Os
X is independently Cl, Br or I
a is an integer 2, 3 or 4
b is an integer 2, 3 or 4
n is an integer of at least 2, preferably up to 1000
m is a charge selected from the group consisting of 0, −1 and −2.

The empirical formula may additionally comprise solvent molecules.

The present invention solves the technical problem defined above by the presence of methyl halide and/or hydrogen halide and at least one compound selected from the group consisting of ruthenium carbonyl halides, osmium carbonyl halides and mixtures thereof in the reaction of methanol and/or dimethyl ether with an olefin.

The methyl halide and/or hydrogen halide is preferably an iodide; that is, the methanol and/or dimethyl ether is preferably reacted with an olefin in the presence of methyl iodide and/or hydrogen iodide.

Methyl iodide may be formed in situ by the reaction of hydrogen iodide with methanol. Hydrogen iodide may be formed in situ by the reaction of methyl iodide with water, which may in turn be formed by the condensation of methanol to form dimethyl ether and water.

When the process of the present invention is performed in the liquid phase, the concentration of methyl halide and/or hydrogen halide is suitably in the range of 0.1 to 1.0 mol/liter.

Thus, the process of the present invention is suitably performed in the liquid phase with methyl iodide and/or hydrogen iodide at a concentration of 0.1 to 1.0 mol/liter of total iodide.

The ruthenium compound may have an empirical formula selected from the group consisting of:

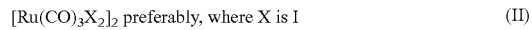

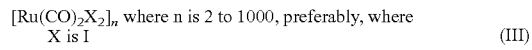

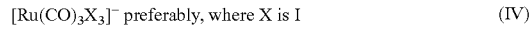

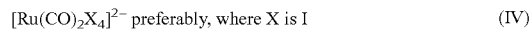

and mixtures thereof.

These ruthenium compounds may be generated in situ by the reaction of $Ru_3(CO)_{12}$ with iodine and/or methyl iodide.

The osmium compound may have an empirical formula selected from the group consisting of:

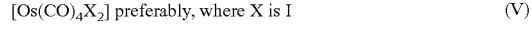

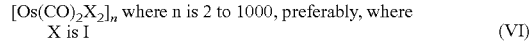

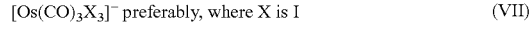

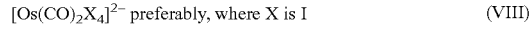

and mixtures thereof.

These osmium compounds may be generated in situ by the reaction of osmium compounds with iodine and/or methyl iodide.

Preferably, the halide of the ruthenium or osmium compound is the same as in the methyl halide and/or hydrogen halide. Preferably, the halide is iodine in the ruthenium or osmium compound and also in the methyl halide and/or hydrogen halide.

When the process of the present invention is performed in the liquid phase, the concentration of ruthenium compounds is preferably in the range of 0.1 to 2.0 mol/liter of ruthenium. When the process of the present invention is performed in the liquid phase, the concentration of osmium compounds is preferably in the range of 0.1 to 2.0 mol/liter of osmium. The concentration may be limited by the solubility of the ruthenium and/or osmium compounds.

A mixture of methanol and dimethyl ether may be used in the process of the present invention. Suitably the molar ratio of methanol:dimethyl ether when a mixture is used, is in the range of 100:1 to 1:100.

The olefin may have a structural formula:

wherein $R^1$, $R^2$, $R^3$ and $R^4$ are independently H or a branched or straight chain alkyl group of 1 to 20 carbon atoms, preferably of 1 to 12 carbon atoms, more preferably of 1 to 10 carbons atoms and most preferably of 1 to 8 carbon atoms.

Preferred olefins for use in the present invention are 2,3 dimethylbut-2-ene which has a formula (VII) in which $R^1$, $R^2$ and $R^3$ are methyl groups and $R^4$ is H; 2-methylbut-2-ene which has a formula (VII) in which $R^1$ and $R^3$ are methyl groups and $R^2$ and $R^4$ are H; propylene which has a formula (VII) in which $R^1$, $R^2$, $R^3$ and $R^4$ are H. The olefin may be provided in a refinery process stream containing butenes, such as a C4 raffinate stream. The olefin may be provided in a raffinate-2 process stream which comprises normal butenes and mixed butanes. Preferably, the raffinate streams do not contain any significant amount of butadiene.

The olefin may be formed in the reactor from a corresponding alkyl alcohol or alkyl halide. Preferably, the alkyl halide has a halogen group which is the same as the X of the $CH_3X$ and/or HX and is more preferably an iodide. Thus, according to this aspect of the invention, an alkyl alcohol or alkyl halide is introduced into the reactor and is converted in the reactor to the olefin which reacts with the methanol and/or dimethyl ether according to the process of the present invention. Preferably, such a reaction is performed at a temperature which facilitates olefin formation. Preferably, such a reaction is performed at a temperature of greater than 130° C.

The process of the present invention produces a reaction product which comprises at least one hydrocarbon which has at least one more methyl group than the olefin reactant.

Thus, the reaction product of 2,3 dimethylbut-2-ene comprises 2,3,3 trimethylbut-1-ene (which is also called triptene). The reaction product of 2-methylbut-2-ene comprises 2,3 di-methylbut-1-ene and/or 2,3 di-methylbut-2-ene. The reaction product of propylene comprises but-1-ene and/or but-2-ene. The reaction product of butenes comprises a mixture of $C_5$ olefins.

The hydrocarbon products produced by the reaction of a reactant selected from the group consisting of methanol, dimethyl ether, methyl acetate and mixtures thereof, with an olefin, may be hydrogenated to produce saturated hydrocarbons. Thus, according to a further aspect of the present invention there is provided a process in which the hydrocarbon product is hydrogenated. This hydrogenation may be performed after removing the hydrocarbon from the reactor or it may be performed in the reactor. An advantage of the use of a ruthenium compound in the process of the present invention is that such a compound may exhibit the ability to catalyse the hydrogenation of the hydrocarbon product in the presence of hydrogen gas. This may provide an advantage of hydrogenating the hydrocarbon product in the reactor without the use of an additional hydrogenation catalyst.

Additionally or alternatively a suitable hydrogenation catalyst may be used which comprises at least one element selected from the group consisting of nickel, ruthenium, iridium, palladium, platinum and mixtures thereof. The hydrogenation catalyst may comprise a support. A suitable support is silica.

Thus, the process of the present invention may be performed in the presence of hydrogen, preferably at a partial pressure in the range of 0 to 100 bar, more preferably at a partial pressure in the range of 0 to 50 bar, and preferably whereby the hydrocarbon product is hydrogenated.

Preferably, the hydrocarbon is removed from the reactor, separated from the methyl halide and/or hydrogen halide and from the ruthenium and/or osmium compound(s) and then hydrogenated.

The process of the present invention also has an advantage that zinc or indium compounds may be absent from the reactor. Also, the process of the present invention has an advantage that rhodium and iridium may be absent from the reactor.

The reaction of the present invention may also produce oxygenated by-products. Thus, for example in the reaction of 2,3 dimethylbut-2-ene with methanol and/or dimethyl ether the reaction product may comprise trimethyl-2-butanol and/or 2,2,3-trimethylmethoxybutane.

When the olefin reacts with methanol, water is produced in addition to the hydrocarbon product. When the olefin reacts with dimethyl ether, methanol is produced in addition to the hydrocarbon product. The methanol may react further to produce water and a further methylation product. When the olefin reacts with methyl acetate, acetic acid is produced in addition to the hydrocarbon product.

If the water produced in the reaction of the present invention causes a reaction mixture to be present in the reactor as two liquid phases, the water may be separated by decantation. The water may be removed by distillation and/or by the use of a drying agent, for example molecular sieve.

The process of the present invention may be performed as a batch or as a continuous process. When operated as a continuous process reactants (methanol, dimethyl ether and/or methyl acetate and olefin) may be introduced continuously together or separately into the reactor and the hydrocarbon product may be continuously removed from the reactor.

The hydrocarbon product may be removed from the reactor in a batch or continuous process together with methyl halide and/or hydrogen halide and ruthenium and/or osmium compounds, these being separated from the hydrocarbon product and other products of the reaction such as for example water, methanol, and oxygenated hydrocarbons, if present, and recycled to the reactor. Unreacted reactants may also be separated from the hydrocarbon product and recycled to the reactor.

The process of the present invention may be performed in the gas or liquid phase, preferably in the liquid phase. More than one liquid phase may be present in the reactor in the process of the present invention, optionally together with at least one solid phase.

The process of the present invention may be performed at a temperature in the range 100 to 300° C., preferably in the range 130 to 200° C.

The process of the present invention may be performed in the presence of carbon monoxide, preferably at a partial pressure in the range of 0.1 to 20 bar, more preferably at a partial pressure in the range of 1 to 5 bar. Carbon monoxide may be lost from the osmium and/or ruthenium carbonyl halide compounds in the process of the present invention. It may be desirable to perform the process of the present invention in the presence of some additional carbon monoxide. This may maintain the activity of the carbonyl halide compounds.

The process of the present invention when performed at a total pressure in the range of atmospheric pressure up to 100 barg.

The invention will now be described with respect to the following examples.

EXAMPLE 1

The following amounts of reagents were used:

| | |
|---|---|
| Methanol | 1.1970 g |
| [Ru(CO)$_4$I$_2$] | 2.1162 g |
| Methyl iodide | 105 μl |
| 2,3-Dimethyl-2-butene | 2.1145 g |

The [Ru(CO)$_4$I$_2$], 2,3-dimethyl-2-butene and then the methanol were weighed into a 15 ml ACE™ glass pressure tube. The tube was then agitated with a spatula and shaken to dissolve the [Ru(CO)$_4$I$_2$], most of which did not dissolved.

No heat was evolved. The methyl iodide was added and the tube sealed. The contents of the tube appeared to have separated into three layers, the bottom layer contained orange solid, whilst the top layer was orange in colour. The middle layer was yellow in colour and appeared to contain suspended solid.

The tube was encased in a mesh, placed in a metal beaker and then placed in an oven at 160° C. for 3 hours.

On cooling, the tube contained a lot of red solid and a clear orange liquid layer. The tube was cooled to room temperature and when opened, it released a lot of pressured gas. The contents continued to bubble so the top was left off for the next 20 hours until the bubbling had stopped.

50 μl of cyclohexane was then added to act as an internal standard, the contents were shaken and allowed to settle. An aliquot (50 μl) was removed and diluted with deuterated trichloromethane (250 μl), CDCl₃, for gas chromatographic (GC) analysis, the results of which are set out in Table 1.

It was observed that the product of the reaction is a hydrocarbon, triptene (identified by NMR by comparison with a standards containing triptane and triptene and GC-MS-fragmentation pattern in the mass spectrum and matching against library spectra). The yield of triptene based upon 2,3-dimethylbut-2-ene fed to the reactor was 23.3%, with a selectivity based upon 2,3-dimethylbut-2-ene converted of 30.3%. Negligible triptane was produced.

The low mass accountability was attributed to loss of light materials on opening the sample.

Analysis by GC-MS showed the presence of dimethyl butanols, trimethyl-2-butanol and 2,2,3-trimethylmethoxybutane.

TABLE 1

GC Analysis of the hydrocarbon products

| Compound | % w/w | Normalised % w/w ** |
|---|---|---|
| dimethyl ether | 0.00 | |
| iso-butane/methanol *** | 0.40 | 0.65 |
| n-butane | 0.03 | 0.05 |
| iso-pentane | 0.00 | 0.0 |
| n-pentane | 0.00 | 0.0 |
| methyl iodide | 3.64 | |
| 2-methyl-2-butene | 0.06 | 0.10 |
| 2,3-dimethylbutane | 6.02 | 9.93 |
| 2-methylpentane | 0.000 | 0.00 |
| 3-methylpentane | 0.00 | 0.00 |
| 2,3-dimethyl-2-butene | 33.13 | |
| 2,3,3-trimethylbut-1-ene (triptene) | 38.83 | 64.07 |
| 2,2,3-trimethylbutane (triptane) | 0.000 | 0.00 |
| cyclohexane (internal standard) | 2.63 | |
| 3-methylhexane | 0.00 | 0.00 |
| n-heptane | 0.000 | 0.00 |
| heavies * | 13.77 | 22.73 |
| 2,3,4-trimethylpentane | 0.15 | 0.24 |
| Hexamethyl benzene | 0.00 | 0.00 |
| Total | 98.65 | 97.77 |
| Balance (unknowns) | 1.35 | 2.23 |

* Total of those with a retention time of greater than 1.9 minutes (excluding hexamethyl benzene, n-heptane & 2,3,4-trimethylpentane), a nominal response factor of 1 was used.
** Normalised to hydrocarbon products (excludes CDCl₃), dimethyl ether, 2,3-dimethylbut-2-ene, methyl iodide and cyclohexane [internal standard])
*** Not possible to distinguish methanol from iso-butane using the GC analysis employed.

This example shows the production of a hydrocarbon by reacting, in a reactor, methanol with an olefin in the presence of methyl iodide and a ruthenium carbonyl halide compound.

In particular, this example shows the production of a hydrocarbon (triptene) by reacting, in a reactor, methanol with an olefin (2,3-dimethylbut-2-ene) in the presence of methyl iodide and a ruthenium carbonyl halide compound having an empirical formula [Ru(CO)₄I₂].

The invention claimed is:

1. A process for the production of a hydrocarbon which process comprises reacting, in a reactor, a reactant selected from the group consisting of methanol, dimethyl ether, methyl acetate and mixtures thereof, with an olefin in the presence of methyl halide and/or hydrogen halide and at least one compound selected from the group consisting of ruthenium carbonyl halides, osmium carbonyl halides and mixtures thereof.

2. A process as claimed in claim 1 in which each ruthenium carbonyl halide or osmium carbonyl halide has an empirical formula:

$$[M(CO)_a X_b]_n^m \quad (I)$$

in which:
M is Ru or Os
X is independently Cl, Br or I
a is an integer 2, 3 or 4
b is an integer 2, 3 or 4
n is an integer of at least 2
m is a charge selected from the group consisting of 0, −1 and −2.

3. A process as claimed in claim 1 in which the methyl halide and/or hydrogen halide is an iodide.

4. A process as claimed in claim 2 in which the ruthenium carbonyl halide has an empirical formula selected from the group consisting of:

$$[Ru(CO)_3 X_2]_2, \text{ where X is I} \quad (II)$$

$$[Ru(CO)_2 X_2]_n \text{ where n is 2 to 1000, and X is I} \quad (III)$$

$$[Ru(CO)_3 X_3]^-, \text{ where X is I} \quad (IV)$$

$$[Ru(CO)_2 X_4]^{2-}, \text{ where X is I} \quad (IV)$$

and mixtures thereof.

5. A process as claimed in claim 2 in which the osmium carbonyl halide has an empirical formula selected from the group consisting of:

$$[Os(CO)_4 X_2], \text{ where X is I} \quad (V)$$

$$[Os(CO)_2 X_2]_n \text{ where n is 2 to 1000, and X is I} \quad (VI)$$

$$[Os(CO)_3 X_3]^-, \text{ where X is I} \quad (VII)$$

$$[Os(CO)_2 X_4]^{2-}, \text{ where X is I} \quad (VIII)$$

and mixtures thereof.

6. A process as claimed in claim 1 in which the olefin has a structural formula $$R^1 R^2 C = C R^3 CH_2 R^4 \quad (VII)$$

wherein R¹, R², R³ and R⁴ are independently H or a branched or straight chain alkyl group of 1 to 20 carbon atoms.

7. A process as claimed in claim 6 in which the olefin is 2,3 dimethylbut-2-ene and the product of the reaction comprises 2,3,3 trimethylbut-1-ene.

8. A process as claimed in claim 1 in which the process is performed in the presence of hydrogen, at a partial pressure in the range of 0 to 100 bar.

9. A process as claimed in claim 1 in which the hydrocarbon product is hydrogenated.

10. A process as claimed in claim 1 in which the process is performed in the presence of carbon monoxide, at a partial pressure in the range of 0.1 to 20 bar.

11. A process as claimed in claim 2 in which n is an integer up to 1000.

12. A process as claimed in claim 6 in which $R^1$, $R^2$, $R^3$ and $R^4$ are independently H or a branched or straight chain alkyl group of 1 to 12 carbon atoms.

13. A process as claimed in claim 6 in which $R^1$, $R^2$, $R^3$ and $R^4$ are independently H or a branched or straight chain alkyl group of 1 to 10 carbons atoms.

14. A process as claimed in claim 6 in which $R^1$, $R^2$, $R^3$ and $R^4$ are independently H or a branched or straight chain alkyl group of 1 to 8 carbons atoms.

15. A process as claimed in claim 8 in which the process is performed in the presence of hydrogen at a partial pressure in the range of 0 to 50 bar.

16. A process as claimed in claim 10 in which the process is performed in the presence of carbon monoxide, at a partial pressure in the range of 1 to 5 bar.

* * * * *